United States Patent [19]

Klug et al.

[11] Patent Number: 4,846,909
[45] Date of Patent: Jul. 11, 1989

[54] METHOD OF APPLING ADHESIVE TO A MALE EXTERNAL URINARY COLLECTION DEVICE

[75] Inventors: Kenneth R. P. Klug; Robert J. Klug, both of Tucson, Ariz.

[73] Assignee: Sierra Laboratories, Inc., Tucson, Ariz.

[21] Appl. No.: 944,668

[22] Filed: Mar. 6, 1987

Related U.S. Application Data

[60] Division of Ser. No. 759,934, Jul. 26, 1985, abandoned, which is a continuation-in-part of Ser. No. 540,379, Oct. 11, 1983, abandoned.

[51] Int. Cl.$^4$ .......................... B44C 1/16; B32B 31/00; A61F 5/44
[52] U.S. Cl. .................................. 156/232; 156/289; 156/294; 156/303.1; 428/36.5; 428/36.8; 604/352
[58] Field of Search ............... 156/230, 232, 240, 249, 156/277, 303.1, 293, 294, 344, 289, 165; 264/264; 427/230, 236, 289; 428/40, 343, 202, 35, 36; 604/346, 347, 349, 351, 352; 128/79, 348.1, 379, 386, DIG. 24

[56] References Cited

U.S. PATENT DOCUMENTS

| | | | |
|---|---|---|---|
| 2,926,699 | 3/1960 | Wulms | 150/294 |
| 3,336,926 | 8/1967 | Gresham | |
| 3,369,546 | 2/1968 | Hickok | |
| 3,520,305 | 7/1970 | Davis | 804/349 |
| 3,608,552 | 9/1971 | Broerman | 604/349 |
| 3,631,857 | 1/1972 | Maddison | 604/349 |
| 3,863,638 | 2/1975 | Rogers, III et al. | 604/352 |
| 4,300,966 | 11/1981 | Hoffmann | 156/303.1 |
| 4,407,686 | 10/1983 | Cook et al. | 156/230 |
| 4,461,663 | 7/1984 | Tachibana et al. | 156/294 |
| 4,475,909 | 10/1984 | Eisenberg | 604/349 |
| 4,475,910 | 10/1984 | Conway et al. | 604/352 |
| 4,540,409 | 9/1985 | Nystrom et al. | 604/349 |

FOREIGN PATENT DOCUMENTS

86/00816 2/1986 PCT Int'l Appl. ............... 604/349

OTHER PUBLICATIONS

URO-SAN PLUS, Mentor article, pp. 1-4, 04-19-82.

Primary Examiner—Michael W. Ball
Assistant Examiner—Louis Falasco
Attorney, Agent, or Firm—David G. Rosenbaum

[57] ABSTRACT

An improved male urinal device comprises an upper thin walled sheath, an intermediate transition zone having a thicker wall, and a lower stem portion having a still thicker wall. The stem portion includes a stem, a bulbous portion above the stem and a conical or funnel section joined to the upper portion of the bulb and to the lower end of the transition zone. A resilient ring of foam cushion material is bonded to an upper portion of the inner surface of the sheath and has a second adhesive surface which engages and forms a seal around the penis.

The present invention also provides a method of applying a suitable adhesive to an inner surface of the male urinal device. The method comprises employing a transfer mandrel having a high release outer coating of a suitable high release material, applying a suitable pressure sensitive adhesive in various patterns, rolling the male urinal device onto the transfer mandrel thereby causing the adhesive to adhere to an inner surface of the male urinal device. Re-rolling of the male urinal device causes the release of the adhesive from the transfer mandrel thereby causing it to be transferred to an inner surface of the male urinal device.

13 Claims, 2 Drawing Sheets

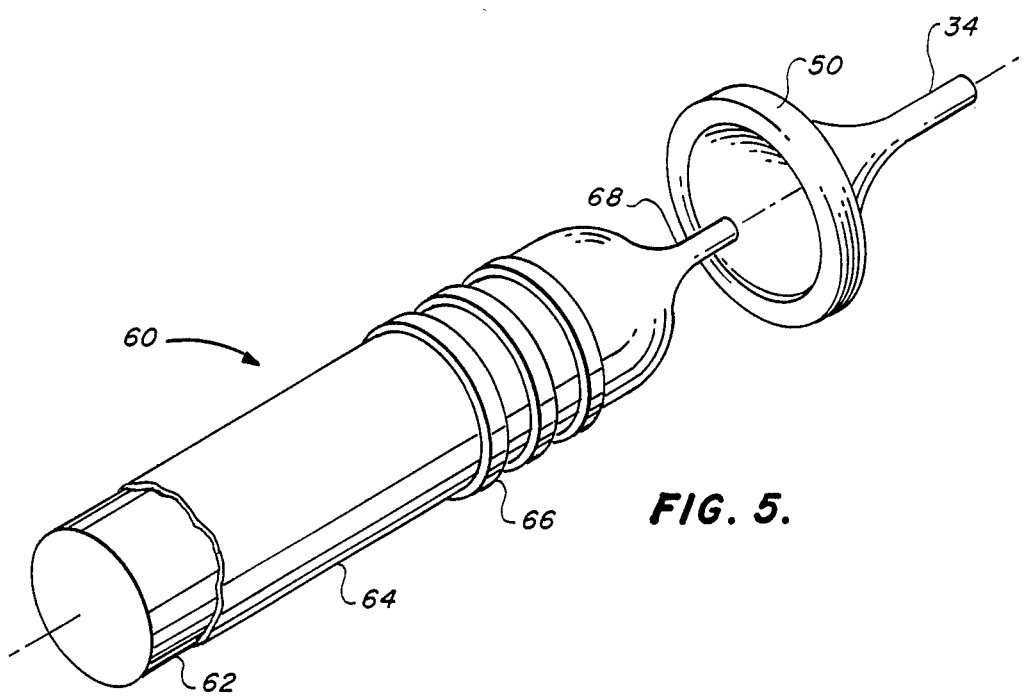
FIG. 5.
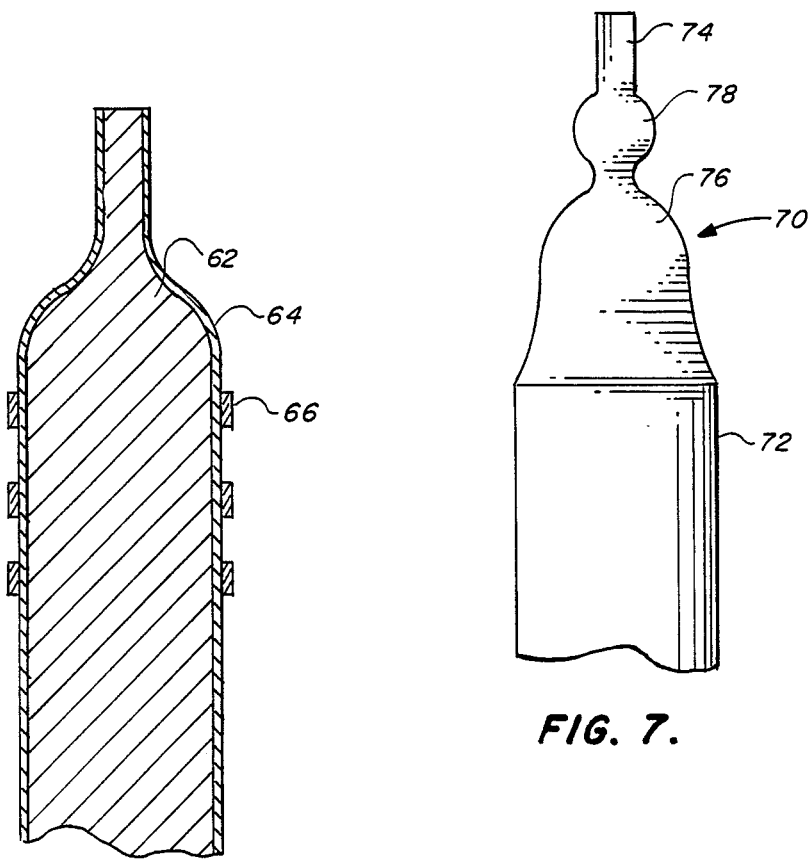
FIG. 6.
FIG. 7.

METHOD OF APPLING ADHESIVE TO A MALE EXTERNAL URINARY COLLECTION DEVICE

CROSS REFERENCES TO RELATED APPLICATIONS

This application is a division of application Ser. No. 759,934, filed July 26, 1985, now abandoned, which is an application is a continuation in part of a prior application Ser. No. 540,379, filed October 11, 1983 now abandoned.

BACKGROUND OF THE INVENTION

1. Field of the Invention

This invention relates generally to a urinal device for use by males having little or no bladder control, and more particularly to an improved male urinal device which does not require elastic single side coated adhesive tape on the outside of the device or a double side coated adhesive tape rolled or spiraled around the penis to produce a good seal thereby preventing the leakage of urine.

There have been numerous attempts to provide a male urinary device which is intended to be functional and yet comfortable, prevent the backup of urine, and insure that urine cannot escape upwardly through the sheath. For example, U.S. Pat. No. 3,835,857 filed Sept. 17, 1974 and entitled "Male Urinal Device" described a male urinal device comprising a urine receptacle which is connected via a flexible tube to a sheath which is adapted to be placed over and secured to the penis of the user. The sheath consists of a thin body portion of resilient material and a relatively large and rigid conical and tubular portions integrally formed with the body portion. A bulbous portion is formed by extending the conical portion in the direction of the body portion sufficiently that the internal diameter of the conical portion where it joins the body portion is greater than the normal diameter of the body portion.

As described in U.S. Pat. No. 3,863,638 filed Feb. 4, 1975 and entitled "Sheath Arrangement for Male Urinal Device", the flexible sheath extends over a substantial lengthwise portion of the penis. A liner pad of synthetic, resiliently compressible, deformable, waterproof material in the form of a relatively wide strip is wound around the penis to form a cushion between the penis and the sheath. It is recommended that the cushion material be long enough to be wrapped at least one and one-half turns around the penis and that it have at least one adhesive surface so as to cling to the penis. A relatively wide tape of elastic material may be wrapped under tension over the sheath to hold the sheath firmly against the liner pad.

It should be appreciated that the deployment of the prior art device is, at best, a cumbersome process, and may represent an almost impossible task to the aged, arthritic and/or obese where the penis may be literally out of sight.

SUMMARY OF THE INVENTION

It is an object of the present invention to provide an improved male device for use by individuals having little or no bladder control.

It is a further object of the present invention to provide a male urinal device which is easy to put on and which is comfortable to wear.

It is a still further object of the present invention to provide an improved male device which includes a tube section which is constructed so as to be free of twists and/or kinks.

It is another object of the present invention to provide a method of making an improved male urinal device.

It is yet another object of the present invention to provide a method of making an improved male urinal device employing a molding mandrel which imparts the optimum configuration to the improved male urinal device.

It is still another object of the present invention to provide a method of making an improved male urinal device employing a transfer mandrel for imparting an adhesive area on an inner surface of the improved male urinal device.

It is a more particular object of the present invention to provide a method of making an improved male urinal device employing a transfer mandrel for imparting an adhesive pattern which optimally creates a leakproof seal between the wearer's skin and the improved male urinal device, without the need of awkward and cumbersome tape wraps.

Yet another object of the present invention is to provide an improved male urinal device which, when put on, will remain in place even during and after vigorous urine discharges.

Still another object of the present invention is to provide an improved male device which may be placed on the penis and prevent the leakage of urine upward through the sheath without requiring the placement of single side coated adhesive tape on the outside of the device or single or double sided adhesive tape rolled or spiraled around the penis.

It is a further object of the present invention to provide an improved male device which provides a better contour when positioned on the penis.

It is a still further object of the present invention to provide an improved male device which includes means for preventing ballooning of the sheath when urine is suddenly discharged from the bladder. Such means also prevents the device from being forced off the penis during vigorous discharges of urine.

According to a broad aspect of the invention there is provided a sheath of flexible material for covering a substantial lengthwise portion of a penis to which said sheath is applied and having a stem portion extending beyond the head of said penis for conducting urine. A resilient ring of cushion material has a first surface joined to an upper portion of the inner surface of said sheath and an adhesive second surface for engaging and forming a seal around said penis, said second adhesive second surface being imparted from a transfer mandrel having a high release coating.

The above and other objects, features and advantages of the present invention will be more clearly understood from the following detailed description taken in conjunction with the accompanying drawings.

BRIEF DESCRIPTION OF THE DRAWINGS

FIG. 5 is a partial sectional perspective view of a transfer mandrel employed in the present invention, showing an adhesive pattern to be transferred to a corresponding male device;

FIG. 6 is a cross-sectional view of the transfer mandrel showing the high release coating employed in the present invention;

FIG. 7 is a side elevational view of a molding mandrel employed in the present invention to make the male device according to the present invention.

DESCRIPTION OF THE PREFERRED EMBODIMENT

Figure 1:
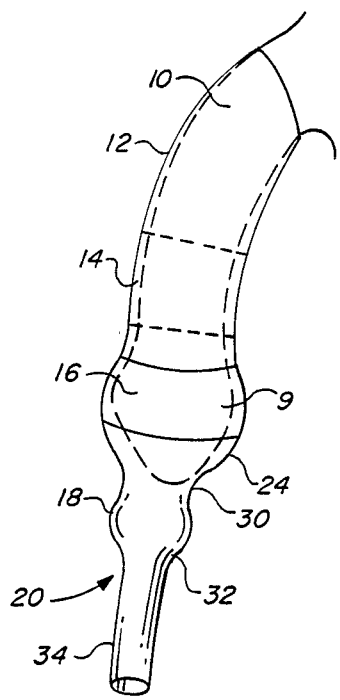
FIG. 1 is a plan view of the inventive male device mounted on a penis.
Figure 2:
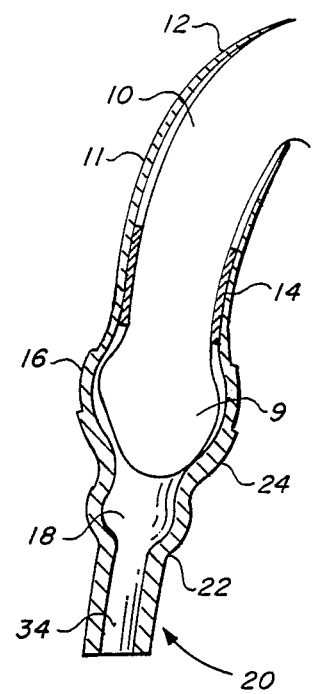
FIG. 2 is a view similar to that shown in FIG. 1 except that the inventive male device is shown in longitudinal cross-section.
Figure 3:
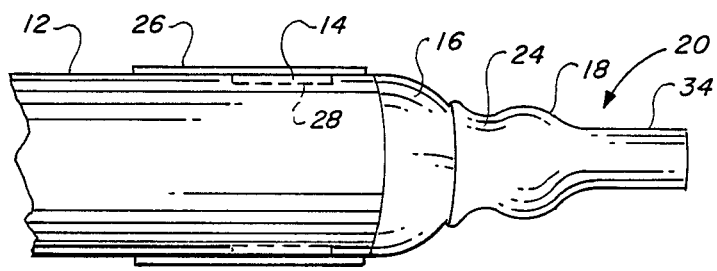
FIG. 3 is another view partly in cross-section of the inventive male device.

Referring to FIGS. 1, 2 and 3, wherein like elements are denoted by like reference numerals, the inventive male device includes a sheath 12 of a flexible, waterproof material, preferably latex. An adhesive 66, FIG. 5 may be foamed onto a transfer mandrel 60, FIG. 5 and thereafter transferred onto and bonded onto the inside surface of sheath 12, thereby forming foam cushion 14. The foam adhesive cushion ring is resilient and conforms to the shape of penis 10 forming a seal thereon which prevents the leakage of urine upward through sheath 12.

Figure 4:
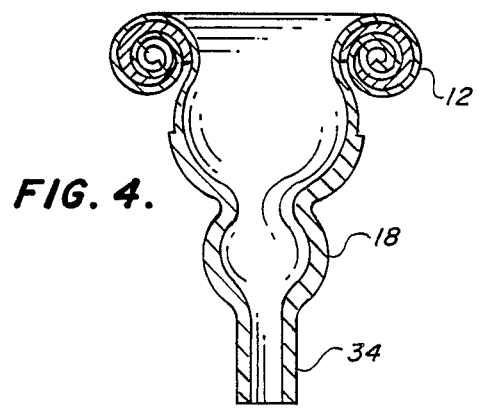
FIG. 4 is a fragmentary cross-sectional view of the inventive device with the sheath portion being rolled up.

As is shown in FIG. 3, sheath 12 has provided along a portion of its length a coating of a non-stick, non-adhesive substance 26 which facilitates unrolling of the device along the penis. As is shown in FIG. 4, the inventive device will be packaged and sold in a rolled configuration which would create certain difficulties were it not for the presence of non-stick layer 26. Layer 26 may, for example be a silicone rubber, or other suitable elastomers, or a teflon coating.

The inventive male device further comprises a relatively rigid stem portion 20 including bulbous portion 18, funnel portion 24 and a stem 34. Bulbous portion 18 is generally sphere like having no sharp angles and has an opening at point 30 which is greater than that at point 32. This facilitates the sudden flow of urine from the bladder and prevents pooling of urine in the bulb. As is well known, a connector plug (not shown) fits into stem 34 so as to couple the catheter to a urine collection bag. It will be appreciated that the tube connecting stem 34 to the bag may have a tendency to twist. Generally spherical bulbous portion 18 strengthens the stem area and resists kinking and twisting of the stem.

The inventive male device employs different sheath wall thicknesses so as to better conform to the shaft and head of the penis 10. First, there is a thin sheath section 11 (e.g., having a wall thickness of approximately 0.006 inches) which provides a comfortable, second-skin feeling to the user. A transition section of the sheath 16 has a relatively greater wall thickness than thin sheath section 11 of approximately 0.02 inches and conforms to the head 9 of penis 10. Finally, stem portion 20 has the relatively greatest wall thickness of approximately 0.05 inches which provides a rigid, non-collapsible stem.

Transition section 16 prevents twisting and provides a better contour than prior art catheters which comprise a relatively thin sheath joined to a rather thick funnel portion. It facilitates placing funnel region 24 close to the tip of penis 10 since the catheter can be rolled further down its length. Finally, transition section prevents ballooning of the sheath when urine is suddenly discharged from the bladder and assists in preventing the catheter from coming off.

In FIG. 5 there is shown a transfer mandrel 60 employed in the making of the male urinal device 50 of the present invention. The transfer mandrel 60 is shown having a generally cylindrical shape, with a blunt end which may or may not have end pin 68 for engaging stem 34 of male device 50. The transfer mandrel 60 has a solid or hollow core 62 which may be made of any suitable material such as plastic or metal, and has a high release, non-adhering material having a very low coefficient of adhesion, such as silicone, teflon or other suitable elastomeric material 64. Alternatively, the entire transfer mandrel may be made of the high release, non-adhering material. The transfer mandrel 60 is coated in the appropriate area with a pattern of medically acceptable pressure sensitive adhesive 66. This adhesive may be foamed so as to form the adhesive cushion 14, FIGS. 1 and 2, but it will be recognized by those skilled in the art that any suitable adhesive may be employed, either in conjuction with or without adhesive cushion 14. A rolled male urinal device 50 is then unrolled onto the transfer mandrel, pressure applied along its length which causes the adhesive to adhere to the inner surface of male urinal device 50. Re-rolling of male urinal device 50 causes the adhesive to be transferred, due to the transfer mandrel's high release coating, to the male urinal device 50.

FIG. 6 is a cross sectional view showing the high release coating 64 of the transfer mandrel 62 and adhesive 66.

FIG. 7 illustrates a molding mandrel 70 used in the formation of male urinal device 50. Salient features are incorporated into the molding mandrel for providing the male urinal device's configuration.

Stem molding portion 74 corresponds to stem portion 34, FIGS. 1,2 of the male urinal device, generally spherical molding portion 78 corresponds to bulbous portion 18, FIGS. 1,2, funnel molding portion 76 corresponds to funnel region 24, F; FIGS 1,2 and sheath molding portion 72 corresponds to sheath portion 10, FIGS. 1,2 of the male urinal device.

The male urinal device is made by placing molding mandrel 70 into the liquid form of the material used to make the male urinal device, such as liquid latex. Molding mandrel 70 is then coated for a sufficient time to create the various section thicknesses. The material is allowed to dry then is rolled off the molding mandrel.

A pressure sensitive adhesive pattern 66 is then laid on transfer mandrel 60. This adhesive may be applied on a high release liner cut to the desired width, which is mechanically applied to the transfer mandrel 60, the liner is then stripped from the adhesive leaving the remaining adhesive 66 on the transfer mandrel. The adhesive may be used with or without a substrate carrier. However, if a substrate carrier is used, it is critical that the substrate have the same degree of elasticity as the sheath of the device. Alternatively, a viscous or solvent based pressure sensitive adhesive may be applied by transfer wheels, spraying or metering through an extrusion head applicator. Ideally, the adhesive will be sufficiently viscous to permit a controlled and uniform application of the adhesive material in a wide variety of patterns onto the transfer mandrel.

The narrow banded strip pattern of the adhesive material 66 shown in FIG. 5 is one embodiment of the present invention.

Alternative embodiments may utilize varying patterns of the pressure sensitive adhesive applied to the transfer mandrel 60. Examples of such patterns include a solid band of adhesive 66 material not greater than two inches in width, or a matrix of dots of the adhesive material 66 may be used so as to create a random dispersion of adhesive points which would lessen the likelihood of skin irritation due to repeated usage of the device.

Thus, there has been described an improved male device which does not require tape rolled around the outside of the device or around the penis. The inventive device merely requires that the pre-rolled device be unrolled. The adhesive foam cushion is automatically applied during the unrolling process and conforms to the shape of the penis.

The above description is given by way of example only. Changes in form and details may be made by one skilled in the art without departing from the scope of the invention as defined by the appended claims.

We claim:

1. A method for producing a self-adhering male urinal device, comprising the steps of:
    providing a transfer mandrel having an outer surface thereof coated with a high release material;
    applying a pattern of adhesive to said transfer mandrel;
    providing a male urinal device comprising a flexible sheath adapted to unroll on a penis and a stem portion in fluid flow communication with said flexible sheath and extending therefrom said male urinal device further having a pattern of a release material for said adhesive applied to said transfer mandrel, said pattern of release material being disposed on an external surface of said unrolled male urinal device and in a position such that, upon re-rolling said male urinal device, said adhesive communicates with said release material;
    engaging said male urinal device onto said transfer mandrel;
    unrolling said male urinal device onto said transfer mandrel;
    exerting pressure on said male urinal device thereby causing said adhesive to adhere to an inner surface of said male urinal device;
    re-rolling said male urinal device thereby causing said adhesive to be released from said transfer mandrel and transferred to said inner surface of said male urinal device.

2. The method according to claim 1, wherein said adhesive comprises any suitable medically acceptable pressure sensitive adhesive.

3. The method according to claim 2, wherein said step of applying said adhesive further comprises employing a foamed adhesive.

4. The method according to claim 2, wherein said adhesive is a viscous water based adhesive.

5. The method according to claim 2, wherein said adhesive is a viscous solvent based adhesive.

6. The method according to claim 1, wherein said step of applying said adhesive further comprises the steps of:
    applying said adhesive to a plurality of transfer wheels; and
    rolling said transfer wheels in such a manner as to transfer said adhesive from said transfer wheels onto said transfer mandrel.

7. The method according to claim 1, wherein said step of applying said adhesive further comprises employing a plurality of spray nozzles to forcibly spray said adhesive onto said transfer mandrel.

8. The method according to claim 1, wherein said step of applying said adhesive further comprises metering said adhesive through an extrusion head applicator onto said transfer mandrel.

9. The method according to claim 1, wherein said step of applying said adhesive further comprises applying said adhesive in a solid band pattern no greater than two inches in width onto said transfer mandrel.

10. The method according to claim 1, wherein said step of applying said adhesive further comprises applying said adhesive in a pattern comprising a plurality of narrow generally parallel bands.

11. The method according to claim 1, wherein said step of applying said adhesive further comprises applying said adhesive in a pattern comprising a random matrix of dots.

12. The method according to claim 1, wherein said step of applying said adhesive further comprises the steps of:
    employing said adhesive on a high release liner;
    placing said adhesive onto said transfer mandrel; and
    stripping away said high release liner.

13. The method according to claim 12, wherein said adhesive on a high release liner further comprises a substrate carrier having the same degree of elasticity as said male urinal device.

* * * * *

UNITED STATES PATENT AND TRADEMARK OFFICE
CERTIFICATE OF CORRECTION

PATENT NO. : 4,846,909

DATED : July 11, 1989

INVENTOR(S) : Klug, et al.

It is certified that error appears in the above-identified patent and that said Letters Patent is hereby corrected as shown below:

In the first line of the title of the patent, delete "APPLING", substitute --APPLYING--.

Signed and Sealed this

Eighth Day of May, 1990

Attest:

HARRY F. MANBECK, JR.

Attesting Officer

Commissioner of Patents and Trademarks